United States Patent
Livingston et al.

(12)

(10) Patent No.: US 6,794,513 B1
(45) Date of Patent: Sep. 21, 2004

(54) PREPARATION OF 3,6-DICHLORO-2-TRICHLOROMETHYLPYRIDINE BY VAPOR PHASE CHLORINATION OF 6-CHLORO-2-TRICHLOROMETHYLPYRIDINE

(75) Inventors: Dana Alan Livingston, Clayton, CA (US); Hawk Suewah Wan, Antioch, CA (US); Kenneth Michael Larson, Walnut Creek, CA (US); Brian John Schoeman, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/793,154

(22) Filed: Mar. 4, 2004

Related U.S. Application Data

(60) Provisional application No. 60/451,801, filed on Mar. 4, 2003.

(51) Int. Cl.[7] ............................................. C07D 213/61
(52) U.S. Cl. ...................................................... 546/345
(58) Field of Search .......................................... 546/345

(56) References Cited

U.S. PATENT DOCUMENTS

| | | | |
|---|---|---|---|
| 3,420,833 A | 1/1969 | Taplin | 260/283 |
| 3,971,799 A | 7/1976 | McGregor | 260/295 |
| 4,087,431 A | 5/1978 | McGregor | 260/295 |
| 4,256,894 A | 3/1981 | Dietsche et al. | 546/345 |
| 4,713,460 A | 12/1987 | DesJardin et al. | 546/345 |
| 4,778,576 A | 10/1988 | Bon et al. | 204/72 |
| 4,939,263 A | 7/1990 | Helling et al. | 546/345 |

*Primary Examiner*—Amelia A. Owens
(74) *Attorney, Agent, or Firm*—Craig E. Mixan

(57) ABSTRACT

A mixture containing 5,6-dichloro-2-trichloromethylpyridine and 3,6-dichloro-2-trichloromethylpyridine enriched in 3,6-dichloro-2-trichloro-methylpyridine is obtained by chlorinating 6-chloro-2-trichloromethylpyridine in the vapor phase using a Type L zeolite catalyst.

9 Claims, No Drawings

PREPARATION OF 3,6-DICHLORO-2-TRICHLOROMETHYLPYRIDINE BY VAPOR PHASE CHLORINATION OF 6-CHLORO-2-TRICHLOROMETHYLPYRIDINE

CROSS-REFERENCE TO RELATED APPLICATIONS

The present application claims the benefit of U.S. Provisional Application Ser. No. 60/451,801 filed Mar. 4, 2003.

FIELD OF THE INVENTION

The present invention concerns a process for the manufacture of 3,6-dichloro-2-trichloromethylpyridine. More particularly, the present invention concerns a process for the manufacture of 3,6-dichloro-2-trichloromethylpyridine by vapor phase chlorination of 6-chloro-2-trichloromethylpyridine in the presence of a Type L zeolite catalyst.

BACKGROUND OF THE INVENTION 3,6-Dichloro-2-trichloromethylpyridine (α,3,6-penta) is a key intermediate for the production of the herbicide clopyralid, 3,6-dichloro-2-pyridinecarboxylic acid. However, α,3,6-penta is difficult to obtain by direct chlorination. U.S. Pat. No. 3,420,833 describes the vapor phase chlorination of α-picoline in which, among a mixture of chlorinated α-picolines of varying degrees of chlorination, α,3,6-penta and 4,6-dichloro-2-trichloromethylpyridine (α,4,6-penta) are produced in a ratio from 0.25 to 0.34. U.S. Pat. No. 4,713,460 discloses the vapor phase chlorination of 2,3-lutidine to provide a mixture of chlorinated picolines and lutidines containing upto 6.8 percent α,3,6-penta U.S. Pat. No. 4,256,894 describes the liquid phase chlorination of 6-chloro-2-trichloromethyl-pyridine (α,6-tet) in the presence of a Lewis acid type catalyst. While a mixture of products is typically obtained, at maximum concentrations of α,3,6-penta, the ratio of α,3,6-penta to 5,6-dichloro-2-trichloromethylpyridine (α,5,6-penta) ranges from 0.18 to 0.53, more typically from 0.34 to 0.38. Even with optimization with respect to the level of α,3,6-penta by removal of HCl as taught in U.S. Pat. No. 4,939,263, the best ratio obtained for α,3,6-penta to α,5,6-penta is 0.55, albeit at relatively low conversion.

Because of the difficulty in obtaining α,3,6-penta by direct chlorination, clopyralid is often manufactured from 3,5,6-trichloro-2-trichloro-methylpyridine (α,3,5,6-hexa) or from 3,4,5,6-tetrachloro-2-trichloromethyl-pyridine (α,3,4,5,6-hepta) by hydrolysis to the corresponding 3,5,6-trichloro- or 3,4,5,6-tetrachloro-2-pyridinecarboxylic acids followed by selective reduction; see U.S. Pat. Nos. 3,971,799; 4,087,431; and 4,778,576.

It would be desirable to have a direct chlorination process with improved selectivity to α,3,6-penta.

SUMMARY OF THE INVENTION

It has now been found that the ratio of α,3,6-penta to α,5,6-penta obtained by chlorination of α,6-tet in the vapor phase can be increased, i.e., the selectivity to α,3,6-penta can be increased, by conducting the chlorination in the presence of a Type L zeolite catalyst. The present invention concerns an improved process for chlorinating 6-chloro-2-trichloromethylpyridine (I)

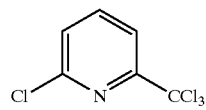

in the vapor phase at elevated temperatures to obtain a chlorination mixture containing 5,6-dichloro-2-trichloromethylpyridine (II) and 3,6dichloro-2-trichloromethylpyridine (III)

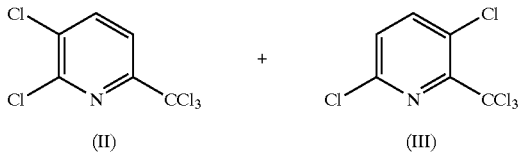

wherin the improvement comprises contacting the 6-chloro-2-trichloromethyl-pyridine (I) with chlorine in the presence of a Type L zeolite catalyst to obtain a mixture enriched in 3,6dichloro-2-trichloromethylpyridine (III). The ratio of α,3,6-penta to α,5,6-penta is greater than 0.75, preferably greater than 1.0. Preferably a Type L zeolite in the K- or [K, Na]-form can be used. Alternatively, the Type L zeolite catalyst can be doped with a Lewis acid catalyst, preferably a zinc containing Lewis acid catalyst, most preferably zinc chloride. Also alternatively, the Type L zeolite can be partly ion exchanged to substitute other elements for potassium. Examples of suitable elements include, but are not limited to Group I and II metal cations.

DETAILED DESCRIPTION OF THE INVENTION

In carryinng out the present invention, α,6-tet and chlorine are contacted in the vapor phase under conditions conducive to monochlorination in the presence of a Type L zeolite catalyst. A mixture containing as the primary product a combination of α,5,6-penta and α,3,6-penta along with varying amounts of other polychloro-2-trichloromethylpyridines and unreacted α,6-tet is obtained.

In carrying out the present invention, vapors of α,6-tet are mixed with an excess over the stoichiometric amount of gaseous chlorine during a brief contact time in the presence of a Type L zeolite catalyst at a temperature of at least 150 to about 350° C. Alternatively, mixed vapors of α,6-tet and an appropriate diluent are mixed with an excess over the stoichiometric amount of gaseous chlorine during a brief contact time in the presence of a Type L zeolite catalyst at a temperature of at least 150 to about 350° C.

The amount of excess chlorine above the stoichiometric is not critical and may vary from stoichiometric to excess chlorine exceeding 400 moles chlorine per mole α,6-tet in the feed. Preferably the amount of excess chlorine above the stoichiometric will be at least 20 moles chlorine per mole α,6-tet in the feed. At 50 moles excess chlorine per mole α,6-tet in the feed, a reduced deactivation rate is seen.

Diluents suitable for carrying out the process of the present invention are materials substantially inert to the action of chlorine under the reaction conditions and include nitrogen, argon, carbon dioxide, perfluorocarbons, perchlorocarbons and perfluorochlorocarbons. Preferred diluents are nitrogen and volatile perchlorohydrocarbons such as carbon tetrachloride and perchloroethylene. Suitable mole ratios of diluent to α,6-tet may vary from about 3:1 to about 200:1.

The vapor phase reaction is conducted at a temperature range from about 150 to about 350° C. The preferred range is from about 175 to about 300° C.

Although residence time is not critical, the reactants should not be allowed to remain in contact with the catalyst for a prolonged period. Residence times generally will not exceed 60 seconds. The preferred time for contact is from about 0.5 to about 15 seconds at temperatures from about 150 to about 300° C.

Operating pressures are not critical and may vary from subatmospheric to superatmospheric. Atmospheric pressure is satisfactory and preferred. Elevated pressures may increase the reaction rates beneficially.

The Type L zeolite catalysts of the present invention, i.e. Linde Type L with the LTL topology, are well known to those skilled in the art and are commercially available from such suppliers as the TOSOH Corporation or The Engelhard Corporation. The typical general molar composition of the Type L zeolite may be expressed as $(K_2,Na_2)O\ Al_2O_3 x SiO_2\ 5\ H_2O$ where=$SiO_2/Al_2O_3$ molar ratio and is generally in the range 5.2–7. The channels are 7.1 angstroms and the channel system may be described as being one dimensional and parallel to the c-axis. Crystal sizes vary and they are a function of the crystallization conditions employed to produce the zeolite. Crystal dimensions are typically <1 micrometers ($\mu$m) and preferably <0.3 $\mu$m. In general, the zeolite is crystallized from a base-stabilized aluminosilicate gel where the silicate may be derived from several silica sources. Examples include potassium and sodium silicates. The alumina source may be derived from several sources including sodium aluminate and alumina hydroxide. The potassium and sodium may be derived from the respective hydroxides. The gels are normally treated at elevated temperatures for periods of time ranging from hours to days. Following hydrothermal treatment, the product is isolated for example, by filtration or centrifugation. The details of the synthesis of the Type L zeolite are well known to those skilled in the art and they are also described in such references as "Zeolite Molecular Sieves", Breck, D. W., R. E. Krieger Publishing Company, (1974).

The Type L zeolite catalysts of the present invention are optionally doped to incorporate a Lewis acid catalyst. Zinc containing Lewis acid catalysts such as $ZnCl_2$ are preferred. The Lewis acid containing Type L zeolite catalysts can be prepared by solid state mixing of the Lewis acid catalyst and the Type L zeolite catalyst followed by calcination at about 550° C. The catalyst may also be prepared by impregnating the zeolite to incipient wetness with a solution of the Lewis acid. This impregnation technique and other impregnation techniques are well known to those skilled in the art. Generally such catalysts contain from about 0.25 to about 10 percent by weight of the Lewis acid. More preferably, the doped Type L zeolite catalysts contain from about 0.5 to about 5 percent by weight of the Lewis acid The Type L zeolite catalyst may also be ion-exchanged with any metal ion or combination of metal ions provided that the resulting ion-exchanged Type L zeolite catalyst is capable of producing a mixture enriched in α,3,6-penta (III). Examples of suitable elements include but are not limited to other Group I metal cations such as Li, Rb and Cs, Group II metal cations such as Mg, Ca, Sr and Ba, lanthanide series metal cations such as La, and transition metal cations such as Fe, Cu and Zn. Ion-exchange is well known in the art and is generally carried out by contacting the material to be ion-exchanged with a solution containing the metal in the form of, for example, a salt or complex. Non-limiting examples include metal halides, preferably the chlorides, nitrates, sulphates and carboxylates, preferably the acetates and lactates. The solvent may be any liquid that is thermally stable under the ion-exchange conditions and inert with respect to the material that is ion-exchanged and the metal ion compound. Water is commonly used as a solvent. The concentration of the metal compound in the solution generally ranges from 0.1 to 8M, and more preferably, from 0.5 to 5M. The material to be ion-exchanged is normally mixed with the soluble metal compound and heated in the temperature range 30 to 120° C. for a time ranging from 30 minutes to 24 hours. Thereafter, the material is separated from the solution, rinsed and dried at a temperature ranging from ambient temperature to 170° C.

The catalysts of the present invention may be bound in various forms with the aid of a binder. There are numerous types of binder available, examples include but are not limited to clays, amorphous silicas and aluminas. The process of forming a bound material is well known to those skilled in the art. Binder loadings are typically less than 30 wt % and preferably less than 20 wt %. The bound catalyst pellets can be of various sizes or shapes. The pellet shape or size is not critical. A typical shape would be cylinders ranging from 1/16 inch to 3/8 inch diameter and lengths ranging from less than half the pellet diameter to 20 times the pellet diameter. Alternative pellet shapes like spheres, tubes, saddles or lobed pellets are all suitable forms.

Before use, the catalysts can optionally be pretreated to remove residual water from their surfaces. Conditioning preferably consists of feeding α,6-tet and diluent together with chlorine over the freshly loaded catalyst bed at reaction tempertures until acid chloride levels produced by the hydrolysis of the trichloromethyl group are diminished. Alternatively the catalyst can be pretreated with $CCl_4$ to remove the water.

Any suitable reactor may be employed. The inlets and outlets as well as the interior surfaces of the reactor must be of materials such as are known to resist corrosion by chlorine and hydrogen chloride at high temperatures. Thus for example, exposed surfaces may be lined with or constructed of nickel, carbon, silica or glass. In practice, it has been found that thermally resistant, high-silica glass, such as Vycor brand, or quartz is satisfactory for small reactors. In large scale apparatus, it is convenient to use a shell of nickel lined with fused silica or a suitable refractory such as carbon. An unlined nickel or nickel alloy reactor is also suitable. To accomplish mixing and introduction of the reactants, the reactor may be fitted with a mixing nozzle for introducing the reactants with substantially simultaneous mixing. Alternatively, the α,6-tet plus diluent and the chlorine may be introduced into the reactor by separate but closely spaced orifaces adjusted so that the chlorine is jetted into the incoming stream of α,6-tet plus diluent. The reactor needs to be partially or substantially filled with the catalyst. Suitable reactor configurations for the reactor include shell and tube reactors, open pipes or fluidized bed reactors. For shell and tube style reactors the catalyst can be placed in either the tube or shell side. This can conveniently allow for control of the reaction temperature by circulation of a heat transfer fluid through the opposite side of the reactor. The proportions for the reactor are not critical. In a preferred form of apparatus, the reactor proper is in the form of a cylinder having a length of 1 to 30 times the diameter. The reactor is partially loaded with catalyst. Conventional accessories such as flowmeters, condensors and scrubbers are also employed.

In carrying out the reaction, α,6-tet plus optionally a diluent are typically introduced into an evaporator to produce vaporized α,6-tet in an inert diluent vapor. Alternatively chlorine gas can be used in the evaporator to produce a vaporized stream with the desired mixture of α,6-tet and chlorine. The evaporator is maintained at a temperture at which rapid vaporization occurs, usually in the range from about 80 to about 250° C., preferably from about 90 to about 210° C. Any vaporizing device may be employed as an evaporator but, for larger scale, a wiped or falling film evaporator is convenient. For efficient operation, it is necessary that the rate of introduction of α,6-tet and/or the temperature of the evaporator be maintained so as to completely vaporize the α,6-tet and to keep it in the vapor state. The mixed vapors from the evaporator are conducted to the reactor where they are contacted with chlorine at a temperature from about 150 to about 350° C., preferably from about 175 to about 300° C., in the presence of the Type L zeolite catalyst. The vapors passing through the reactor are cooled or quenched to separate the chlorinated picoline products from the gaseous chlorine and by-product hydrogen chloride. The desired α,3,6-penta is separated from the chlorinated picoline products and any unconverted α,6-tet by conventional techniques such as fractional distillation. Any unreacted α,6-tet can be separated from the α,3,6-penta and recycled to the reactor. In small scale equipment the reactor exit gases can be characterized using gas chromatography.

In use, the catalyst may decline in reactivity or selectivity relative to its initial performance. The catalyst can be regenerated by removing it from the reactor and placing it in a quartz boat exposed to air while heating in a tube furnace. The preferred time temperature profile starts by heating to 150° C. over a 1 hour time period. Then heating continues at about 10° C./min, stops at 500° C., and remains there for 2.5 hours. Alternatively, the catalyst can be regenerated in situ by correctly heating the deactivated catalyst while exposing it to a suitable oxidizing source such as air humidified at 25° C. Alternative oxidants such as ozone, nitrous oxide or chlorine may also be used.

The following examples illustrate the invention.

EXAMPLES

Preparation of Catalyst A: 1 wt % $ZnCl_2$ on zeolite L by Impregnation to Incipient Wetness $ZnCl_2$ (0.2 gram (g); Aldrich) was dissolved in HCl-acidified deionized water and then added to 20 g Type L zeolite (Engelhard Corporation, EZ-200). The paste was mixed well with a spatula and then dried overnight in air at 80° C. The dry powder was pressed in a cold isostatic press [20,000 pounds per square inch (psi)] and then crushed and sieved to obtain a 14/30 mesh fraction. The 14/30 mesh fraction was calcined in air in a muffle furnace by ramping the temperature from room temperature to 550° C. over 2 hours and then holding at 550° C. for 8 hours, afterwhich the catalyst was allowed to cool to ambient temperature.

Preparation of Catalyst B: Pressed form of Type L Zeolite with no Binder

Type L zeolite (20 g; TOSOH, HSZ-500KOA Lot#50KA1103) was pressed in a cold isostatic press (20,000 psi) and then the solid was crushed and sieved. The 14/30 mesh fraction was recovered and calcinied as described in the Preparation of Catalyst A.

Preparation of Catalyst C: Bound form of Type L Zeolite with 17 wt % Silica Binder Type L zeolite (20 g; Engelhard, EZ-200) was mixed with 4.0 g Aerosil™ 200 (Degussa fumed silica) and sufficient deionized water to form a slurry. The paste was dried at 90° C. overnight and then crushed to a fine powder. The powder was pressed in a cold isostatic press (20,000 psi) and then the solid was crushed and sieved. The 14/30 mesh fraction was recovered and calcined as described in the Preparation of Catalyst A.

Preparation of Catalyst D: Li ion-exchanged Type L Zeolite with 17 wt % Silica Binder Lithium acetate (26.69 g; Aldrich) was combined with 450 g deionized water in 3-necked 500 milliliter (mL) flask equipped with a reflux condensor. The solids were dissolved with stirring and 15 g of Tosoh Type L zeolite (HSZ-500KOA Lot#50KA1103) was added. The contents were heated to 90° C. in oil bath for 24 hours while being stirred at 350 revolutions per minute (rpm). The contents were then cooled and centrifuged in low-speed centrifuge at 3000 rpm for 30 minutes. The supernatant was decanted and the solids were re-suspended in 750 mL deionized water. The rinse and centrifuge procedure was repeated until a total of 4,500 mL of de-ionized water was used as rinse water. Finally, the solids were separated by high-speed centrifugation at 14,000 rpm for 2 hours. The supernatant was decanted and the solid sample was dried in air at 80° C. overnight. The dried zeolite was mixed with Aerosil 200 binder (Degussa) to obtain a 20% amorphous silica content. Sufficient de-ionized water was added to form a thick paste. The paste was dried at 80° C. overnight. The dried sample was pressed in a cold isostatic press at 15,000 psi and the solid was then crushed and sieved to 14/30 mesh. The 14/30 mesh sample was calcined as described in the Preparation of Catalyst A.

Cs-ion exchanged and Rb-ion exchanged Type L zeolites were likewise prepared.

Preparation of Catalyst E: Bound form of Type L Zeolite with 13.5 wt % Alumina Binder Type L zeolite (20 g; Engelhard, EZ-200) was mixed with 4.0 g Catapal™ A (The Vista Chemical Company) and sufficient deionized water to form a slurry. The paste was dried at 90° C. overnight and then crushed to a fine powder. The powder was pressed in a cold isostatic press (20,000 psi) and then the solid was crushed and sieved. The 14/30 mesh fraction was recovered and calcined as described in the Preparation of Catalyst A.

Catalyst Evaluation Test Method Example 1: Standard Operating Conditions

Nitrogen was flow-controlled at a rate of 10.00 standard cubic centimeters per second ($cm^3$/min) over the headspace of tube-shaped glass evaporators containing α-6-tet. The evaporator temperature was controlled at 100° C. with a GC convection oven to give desired α-6-tet vapor pressure of 0.003 atmospheres (atm). The α-6-tet and nitrogen sweep gas then mixed with chlorine that was flow controlled at 5.00 standard $cm^3$/min, and then fed to a GC oven containing rod-shaped glass reactor tubes of 0.25 inch O.D. partially filled with catalyst. The catalyst beds ranged from 0.10–0.60 g and 1.5–7.0 centimeters (cm) in length. The reactor temperature was controlled at designated temperatures (175–325° C.) with a GC convection oven. The product streams from the reactor were sent to an organic trap/vent system. The organics trap system consisted of a glass alligator flask with overhead tubing that sent residual chlorine to glass scrubber bottles containing 10% caustic. Samples from the product stream were analyzed by gas chromatography. The scrubber system was open to atmospheric pressure.

Before generating catalytic conversion data, all the catalysts were pretreated to remove residual water from the surfaces. The conditioning consisted of feeding the α-6-tet/nitrogen sweep and $Cl_2$ over the freshly loaded catalyst bed at 10.00 and 5.00 standard $cm^3$/min, respectively. The reactor temperature was set at 175° C. The conditioning process was monitored by GC-Mass Spec Analysis and typically lasted from 1–5 hours. Complete conditioning was indicated by diminished acid chloride levels.

Catalyst Evaluation Test Method Example 2: Elevated Pressures

The reactor of Example 1 was modified to run at higher pressures with a flow restrictor valve system on the reactor outlet directly before the organics trap. Back pressure ranging from 0–20 psig was applied with extra nitrogen and throttled down with a needle valve. The evaporator temperature was raised to 116° C. to give desired α-6-tet vapor pressure of 0.0064 atm. In addition, the glass reactor tubes and evaporator vials were replaced with stainless steel due to the elevated pressure. All other conditions were similar to Example 1 including nitrogen and chlorine flows, reactor temperature range, the analytical system, and the organic trap conditions.

Catalyst Evaluation Test Method Example 3: Co-feed Testing for Diluent Inertness The reactor of Example 1 was modified to run with alternative diluents. An additional feed was added. In addition to the nitrogen that was flow controlled over the α-6-tet, a second nitrogen supply was flow controlled at 5.0 standard $cm^3$/min over carbon tetrachloride at 0° C. This gave a desired $CCl_4$ vapor pressure of 0.044 atm. Chlorine along with the α-6-tet and nitrogen stream and the $CCl_4$ and nitrogen stream were mixed and then fed to a GC oven containing rod-shaped glass reactor tubes like those in Example 1.

Catalyst Evaluation Test Method Example 4: Chlorine ONLY System

The reactor of Example 1 was modified to run with alternative carrier gases. Instead of nitrogen, chlorine was flow-controlled at a rate of 10.00 standard $cm^3$/min over the headspace of tube-shaped glass evaporators containing α-6-tet. The evaporator temperature was controlled at 100° C. with a GC convection oven to give desired α-6-tet vapor pressure of 0.003 atm. The α-6-tet and chlorine were then fed directly to a GC oven containing rod-shaped glass reactor tubes.

Catalyst data are provided in Table 1.

TABLE 1

| Run | Test Method | Catalyst | Bed Wt (g) | Bed Length (cm) | Temp. (° C.) | Pressure (psig) | Time Online (hrs) | Conv (%) | % 3,6 Penta | % 5,6 Penta | 3,6:5,6 Ratio |
|---|---|---|---|---|---|---|---|---|---|---|---|
| 1 | 1 | A | 0.3204 | 5.5 | 200 | 0.5 | 12.5 | 23.0 | 61.0 | 30.0 | 2.03 |
| 2 | 4 | B | 0.3849 | 4.7 | 200 | 0.5 | 10.5 | 68.0 | 59.0 | 24.0 | 2.46 |
| 3 | 3 | B | 0.3373 | 4.6 | 200 | 0.5 | 11.0 | 31.8 | 46.5 | 19.5 | 2.38 |
| 4 | 1 | E | 0.301 | 4 | 200 | 0.5 | 31.0 | 30.5 | 63.6 | 28.2 | 2.26 |
| 5 | 2 | C | 0.3006 | 3.9 | 200 | 20.0 | 13.0 | 39.5 | 26.3 | 9.3 | 2.83 |
| 6 | 1 | C | 0.3083 | 4.0 | 250 | 0.5 | 5.0 | 43.5 | 49.0 | 29.2 | 1.68 |
| 7 | 1 | D-U | 0.2565 | 3.8 | 200 | 0.5 | 8 | 14.0 | 9.25 | 3.2 | 2.94 |
| 8 | 1 | D-Cs | 0.2540 | 3.0 | 200 | 0.5 | 8 | 7.6 | 2.7 | 3.5 | 0.76 |
| 9 | 1 | D-Rb | 0.2509 | 3.0 | 200 | 0.5 | 8 | 15.4 | 7.3 | 6.1 | 1.2 |
| 10 | 1 | C | 0.3093 | 4.1 | 175 | 0.5 | 4.0 | 22.2 | 72.1 | 9.9 | 7.27 |
| 11 | 1 | blank | | | 250 | 0.5 | 10.0 | 26.6 | 4.9 | 10.5 | 0.46 |
| 12 | 1 | silica | | | 250 | 0.5 | 2.0 | 12.1 | 9.1 | 19.0 | 0.48 |

What is claimed is:

1. An improved process for chlorinating 6-chloro-2-trichloro-methylpyridine (I)

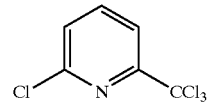

(I)

in the vapor phase at elevated temperatures to obtain a chlorination mixture containing 5,6-dichloro-2-trichloromethylpyridine (II) and 3,6-dichloro-2-trichloromethylpyridine (III)

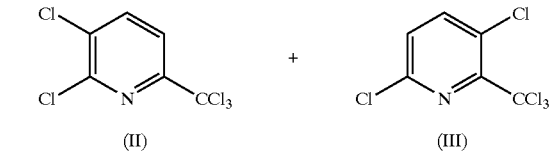

(II)  (III)

wherin the improvement comprises contacting the 6-chloro-2-trichloromethyl-pyridine (I) with chlorine in the presence of a Type L zeolite catalyst to obtain a mixture enriched in 3,6-dichloro-2-trichloromethylpyridine (III).

2. The process of claim 1 in which the ratio of 3,6-dichloro-2-trichloromethylpyridine (III) to 5,6-dichloro-2-trichloromethylpyridine (II) is greater than 0.75.

3. The process of claim 1 in which the ratio of 3,6-dichloro-2-trichloromethylpyridine (III) to 5,6-dichloro-2-trichlormethylpyridine (II) is greater than 1.0.

4. The process of claim 1 in which the temperature is from about 150 to about 350° C.

5. The process of claim 1 in which the Type L zeolite is in the K- or [K, Na]-form.

6. The process of claim 1 in which the Type L zeolite catalyst is doped with a Lewis acid catalyst.

7. The process of claim 1 in which the Type L zeolite catalyst is partly ion exchanged to substitute other elements for potasium.

8. The process of claim 1 in which the Type L zeolite catalyst is regenerated by heating in the presence of a suitable oxidizing source.

9. The process of claim 1 in which the Type L zeolite catalyst is regenerated by heating in the presence of air that has been humidified by contact with 25° C. water.

* * * * *